(12) United States Patent
Lee et al.

(10) Patent No.: US 8,273,873 B2
(45) Date of Patent: *Sep. 25, 2012

(54) SUCROSE OF NEW CONFORMATIONAL POLYMORPHS AND MANUFACTURING METHOD THEREOF

(75) Inventors: Tu Lee, Flushing, NY (US); Gen-Da Chen, Miaoli County (TW)

(73) Assignee: National Central University, Jhongli (TW)

( * ) Notice: Subject to any disclaimer, the term of this patent is extended or adjusted under 35 U.S.C. 154(b) by 379 days.

This patent is subject to a terminal disclaimer.

(21) Appl. No.: 12/586,338

(22) Filed: Sep. 21, 2009

(65) Prior Publication Data

US 2010/0317845 A1    Dec. 16, 2010

(30) Foreign Application Priority Data

Jun. 10, 2009 (TW) ............................... 98119464 A

(51) Int. Cl.
- C13K 5/00 (2006.01)
- C13K 7/00 (2006.01)
- C07H 1/00 (2006.01)
- C07H 3/00 (2006.01)
- C08B 37/00 (2006.01)

(52) U.S. Cl. .................................. 536/123.13; 536/124
(58) Field of Classification Search ............. 536/123.13, 536/124
See application file for complete search history.

(56) References Cited

U.S. PATENT DOCUMENTS

2011/0003983 A1 * 1/2011 Lee et al. ..................... 536/124

FOREIGN PATENT DOCUMENTS

JP         2003-319800       * 11/2003

OTHER PUBLICATIONS

Rouhi, A.M. (2003) The Right Stuff: From research and development to the clinic, getting drug crystals right is full of pitfalls. Chemical & Engineering News, vol. 81, No. 8.*
Brittain, H.G. (1999) Polymorphism in Pharmaceutical Solids—Drugs and the Pharmaceutical Sciences. Published by Marcel Dekker, Inc., New York, p. 1, 2, 178, 179, 185, 219 and 236.*
Thompson, M.D. (1999) "Chemical Development of the Drug Substance Solid Form" in Process Chemistry in the Pharmaceutical Industry. Edited by Gadamasetti, K.G., published by Marcel Dekker, Inc., p. 371-374.*
Machine translation of JP 2003-319800 (2003) [online] [Retrieved Dec. 15, 2010] Retrieved from the internet <http://dossier1.ipdl.inpit.go.jp/AIPN/odse_top_dn.ipdl?N0000=7400>.*
Lee, et al., Dimorphs of Sucrose, Int'l Sugar Journal, 2007, vol. 109, No. 1303, pp. 440-445, online publication, Sep. 2, 2008.

* cited by examiner

*Primary Examiner* — Scarlett Goon
(74) *Attorney, Agent, or Firm* — Hudak, Shunk & Farine Co. LPA

(57) ABSTRACT

A sucrose of a conformational polymorph and its manufacturing method are disclosed. The sucrose is a Form II sucrose having a melting point of 140-180° C., and furfuryl alcohol is added into a saturated sucrose solution by a reverse solution method, such that the saturated solution is recrystallized to form a new sucrose. The sucrose of this conformational polymorph has a melting point lower than the melting point of a general Form I sucrose, and the solubility of the Form II sucrose is different from the solubility of the Form I sucrose. Thus the Form II sucrose can be used as an excipient of medicines, sacrificial fiber blood vessel network structure for cell cultivations, or the manufacture of an optical interference wavy device. Since the hydrogen bonds in the molecular structure of the Form II sucrose and the Form I sucrose are different, the mechanoluminescence of the sucrose is affected.

2 Claims, 6 Drawing Sheets

SUCROSE OF NEW CONFORMATIONAL POLYMORPHS AND MANUFACTURING METHOD THEREOF

BACKGROUND OF THE INVENTION

1. Field of the Invention

The present invention relates to sucrose, in particular to a sucrose of two conformational polymorphs and its manufacturing method.

2. Description of the Related Art

At present, sucrose is one of the best sweet tasting ingredients, due to the advantages of its abundant production, good taste and high manufacturing stability, and thus sucrose is suitable to be used as a cooking condiment, a beverage additive, or a baking additive, and becomes a necessity of our living as well as an important raw material for the food industry. With the properties of easy digestion and quick absorption, sucrose is a very good source of calories. In addition, sucrose has a high content of hydroxyl groups (as shown in FIG. 1) and a strong hydrophilic property, and thus it is easily soluble in water, and the solubility increases with temperature and such characteristic facilitates the manufacture of food. In addition, the annual production of sugar in Taiwan is approximately 60000 tons plus the production of sugar in places all over the world, sugar closely related with food is used extensively in the food industry, and sucrose is also used as an excipient in the medicine industry. Obviously, sucrose plays an important role in our daily life.

The present sugar industry generally manufactures sucrose by processes of cooking sugar and evaporating water to form a saturated solution and then lowering the temperature of the saturated solution, but such manufacturing method requires a high consumption of energy source. In journals related to sucrose, it is found that sucrose only has one morph (Form I) and a melting point maintained at a range of 180-190° C. as shown in FIG. 2. Journals also indicate that the formation of sucrose having a lower melting point is not caused by an impurity such as a mineral or water added in a sugar manufacturing process or a stirring speed. In an article entitled "Dimorphs of Sucrose" and published in International Sugar Journal by Tu Lee and Yu Sheng Lin in 2007, a methyl alcohol reverse solution method is provided for manufacturing another type of sucrose of a new conformational polymorphs and having a low melting point, and the manufactured sucrose does not come with a single morph. More specifically, measurements of this type of sucrose made by a differential scanning calorimetry (DSC) indicate that two endothermic peaks are detected at 150° C. and 185° C. respectively as shown in FIG. 2.

SUMMARY OF THE INVENTION

It is a primary objective of the present invention to solve the sucrose purity and non-single morph issues of the prior art by providing a sucrose of a new conformational polymorph. The present invention is characterized in that a reverse solution method is used, wherein a furfuryl alcohol is added into a saturated sucrose solution, such that the saturated solution is recrystallized to form a purified Form II sucrose of the conformational polymorph. This sucrose has a melting point of 140-180° C. and its differential scanning calorimetry (DSC) shows only one peak, and sucrose of this sort can be used as a medicine excipient.

Another objective of the present invention is to provide a manufacturing method of a sucrose of a new conformational polymorph, and the method comprises the steps of: adding a Form I sucrose in water at a predetermined temperature, such that the sucrose is dissolved into a crystal-free saturated solution; preheating a furfuryl alcohol; adding the furfuryl alcohol into the saturated solution, and stirring the solution uniformly into a mixed solution; maintaining the mixed solution at the predetermined temperature to recrystallize the mixed solution into a new crystallized sucrose; and filtering the mixed solution and dry baking the new crystallized sucrose to obtain a Form II sucrose of the conformational polymorph in accordance with the present invention, wherein the predetermined temperature is 40-80° C. preferably 55-65° C. and the furfuryl alcohol is preheated at the same predetermined temperature.

The sucrose of a new conformational polymorph and its manufacturing method in accordance with the present invention has one or more of the following advantages:

(1) A general sucrose has a single morph (Form I), and the present invention uses a reverse solution method to add a furfuryl alcohol into a saturated sucrose solution to recrystallize the saturated solution into a Form II sucrose, and further uses this method to control the sucrose of a new conformational polymorph.

(2) The method of the present invention is used for crystallizing the Form II sucrose having a melting point of 140-180° C. which is lower than the melting point (180-190° C.) of the original pure Form I sucrose. As to applications, sucrose with a lower melting point can be used as a medicine excipient or a carrier for medicine, and the solubility of the sucrose with a lower melting point is different from the solubility of a general sucrose, and thus the sucrose with a lower melting point has more effect of being an excipient. In addition to the elimination of a bitter taste, sucrose also can be used to achieve the effects of controlling the release speed of a medicine and reducing the consumption of other excipients to lower the cost of excipients.

(3) The method of the present invention is used for recrystallizing a Form II sucrose to be used in a sacrificial fiber blood vessel network structure for cell cultivations, since the manufacturing method forms a marshmallow and then adds a polymer material. In addition, the hydrogen bonds in the molecular structures of the Form II sucrose of the present invention and the general Form I sucrose are different, and thus will affect the mechanoluminescence of the sucrose. The invention can be used for manufacturing an optical interference wavy device.

(4) The present invention improves the sucrose manufactured by a reverse solution method of methyl alcohol as disclosed in the journal "Dimorphs of Sucrose" published by Tu Lee and Yu Sheng Lin. Particularly, related differential scanning calorimetries (DSC) show that the method of the present invention has a better effect and can produce a pure sucrose of a conformational polymorph with a lower melting point and a single morph, and whose differential scanning calorimetry (DSC) shows only one peak.

(5) The method of the present invention can be used for purification, since a concomitant polymorph is impractical for medicines, and thus the purification technology becomes very important, and the novel technology of the present invention has taken a big leap over the prior art to develop another new material of sucrose.

DETAILED DESCRIPTION OF THE PREFERRED EMBODIMENTS

Figure 4:
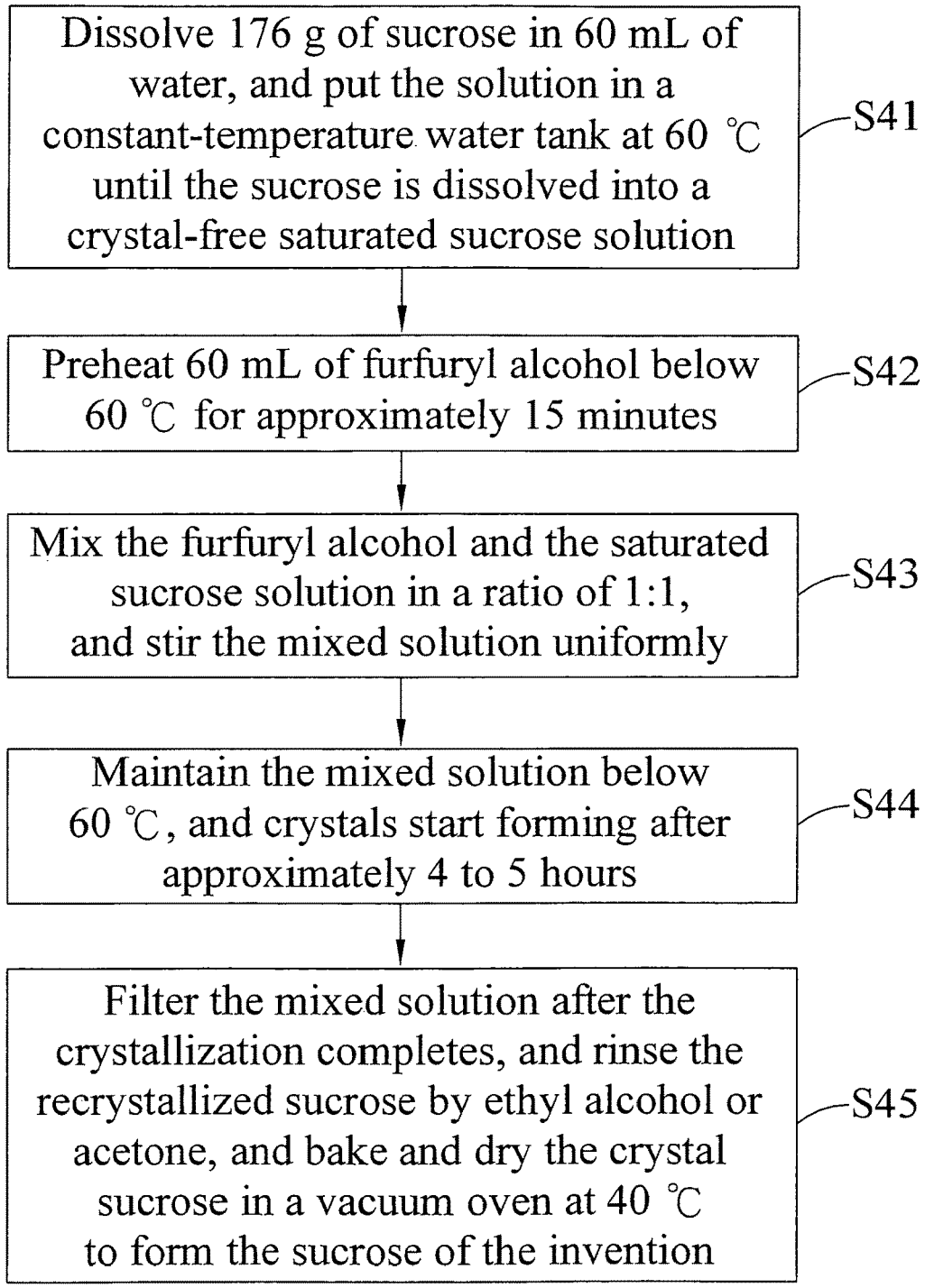
FIG. 4 is a flow chart of a manufacturing method of a sucrose of a new conformational polymorph in accordance with a preferred embodiment of the present invention.

With reference to FIG. 4 for a flow chart of a manufacturing method of a sucrose of a new conformational polymorph in accordance with a preferred embodiment of the present invention, the manufacturing method comprises the following steps:

In Step S41, dissolve 176 g of sucrose in 60 mL of RO water, and maintain a water tank at a constant temperature below 60° C. until the sucrose is dissolved into a crystal-free saturated sucrose solution, since the solubility of saturated Form I sucrose in water below 60° C. is equal to 2873 mg/mL. In Step S42, preheat 60 mL of furfuryl alcohol below 60° C. for approximately 15 minutes. In Step S43, mix the furfuryl alcohol and the saturated sucrose solution in a ratio of 1:1, and stir the mixed solution uniformly by a rotation speed of 500 rpm. In Step S44, maintain the mixed solution at 60° C., and crystal starts forming after approximately 4 to 5 hours. In Step S45, turn off the power of the constant-temperature water tank, and lower the temperature to room temperature naturally, and maintain this state for three days until the crystallization completes, and filter the mixed solution, and rinse the recrystallized sucrose by ethyl alcohol or acetone, and bake the crystal sucrose in a vacuum oven at 40° C. for 24 hours to obtain a Form II sucrose of a new conformational polymorph in accordance with the present invention.

Figure 5:
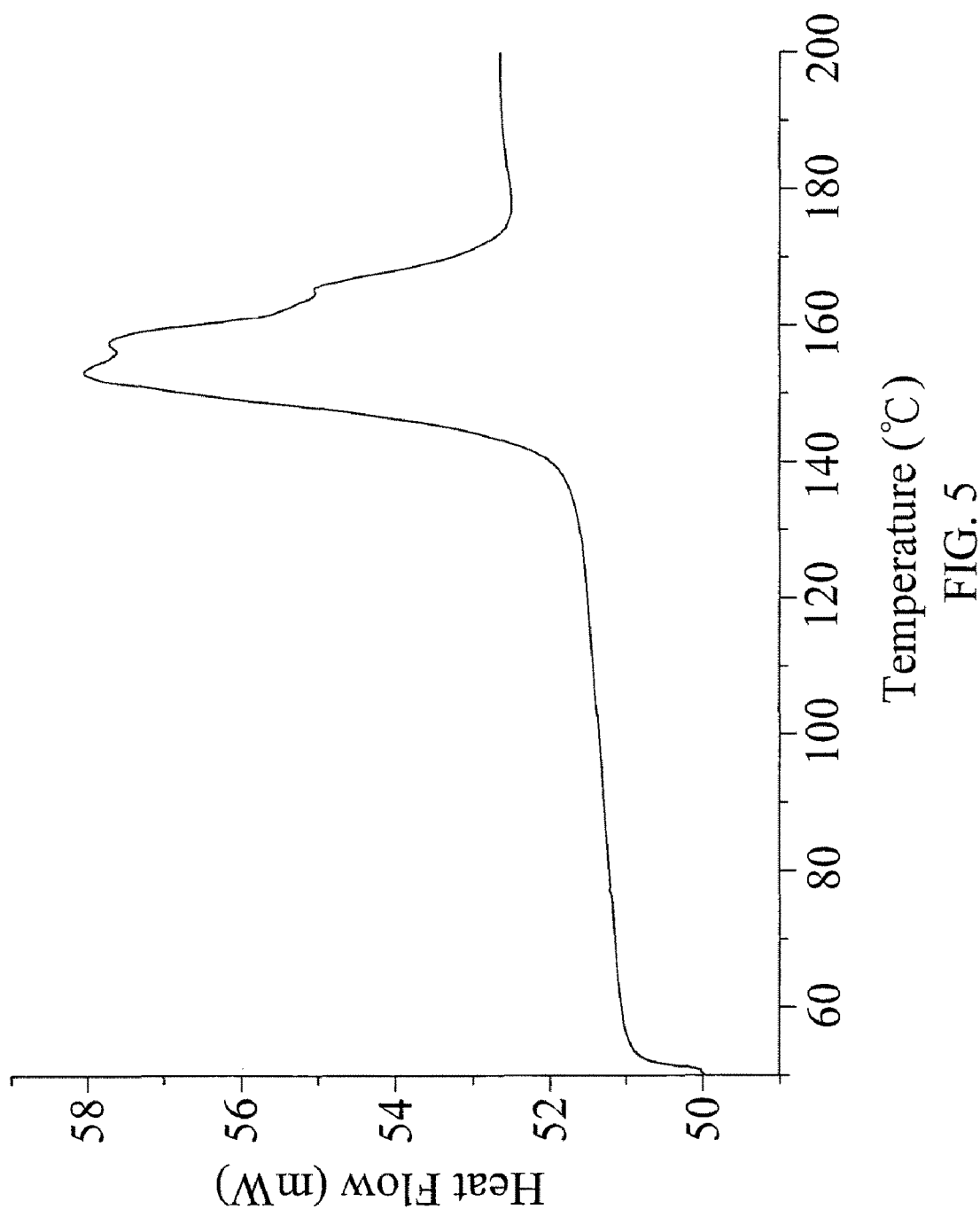
FIG. 5 is a differential scanning calorimetry (DSC) of a sucrose of a new conformational polymorph in accordance with the present invention.

With reference to FIG. 5 for a differential scanning calorimetry (DSC) of a sucrose of a new conformational polymorph in accordance with the present invention, the differential scanning calorimetry (DSC) of the Form II sucrose obtained by the manufacturing method of the present invention shows a single endothermic peak detected at approximately 150° C., and its melting point is 140-180° C.

Figure 1:
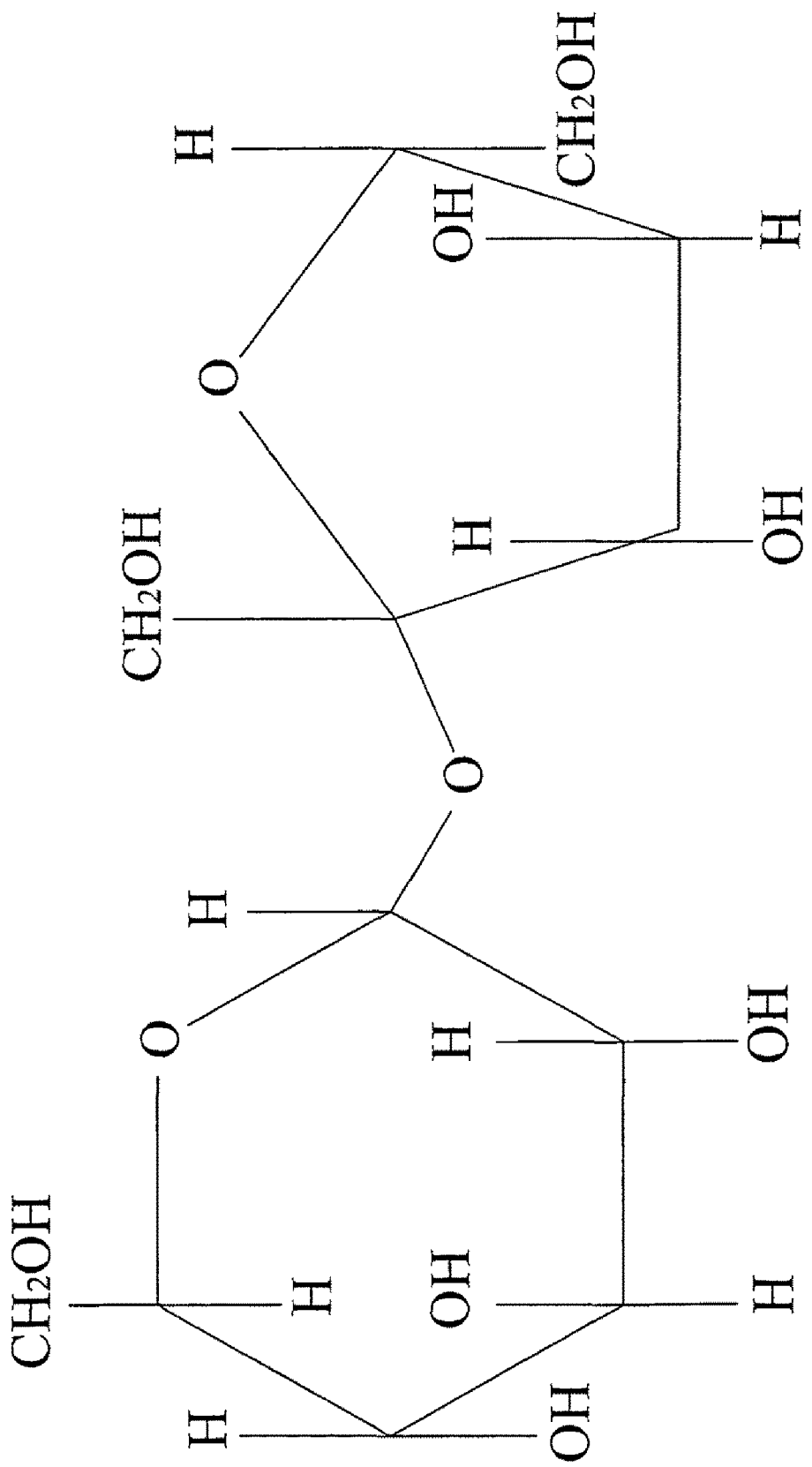
FIG. 1 is a schematic view of a chemical structure of a traditional sucrose.
Figure 2:
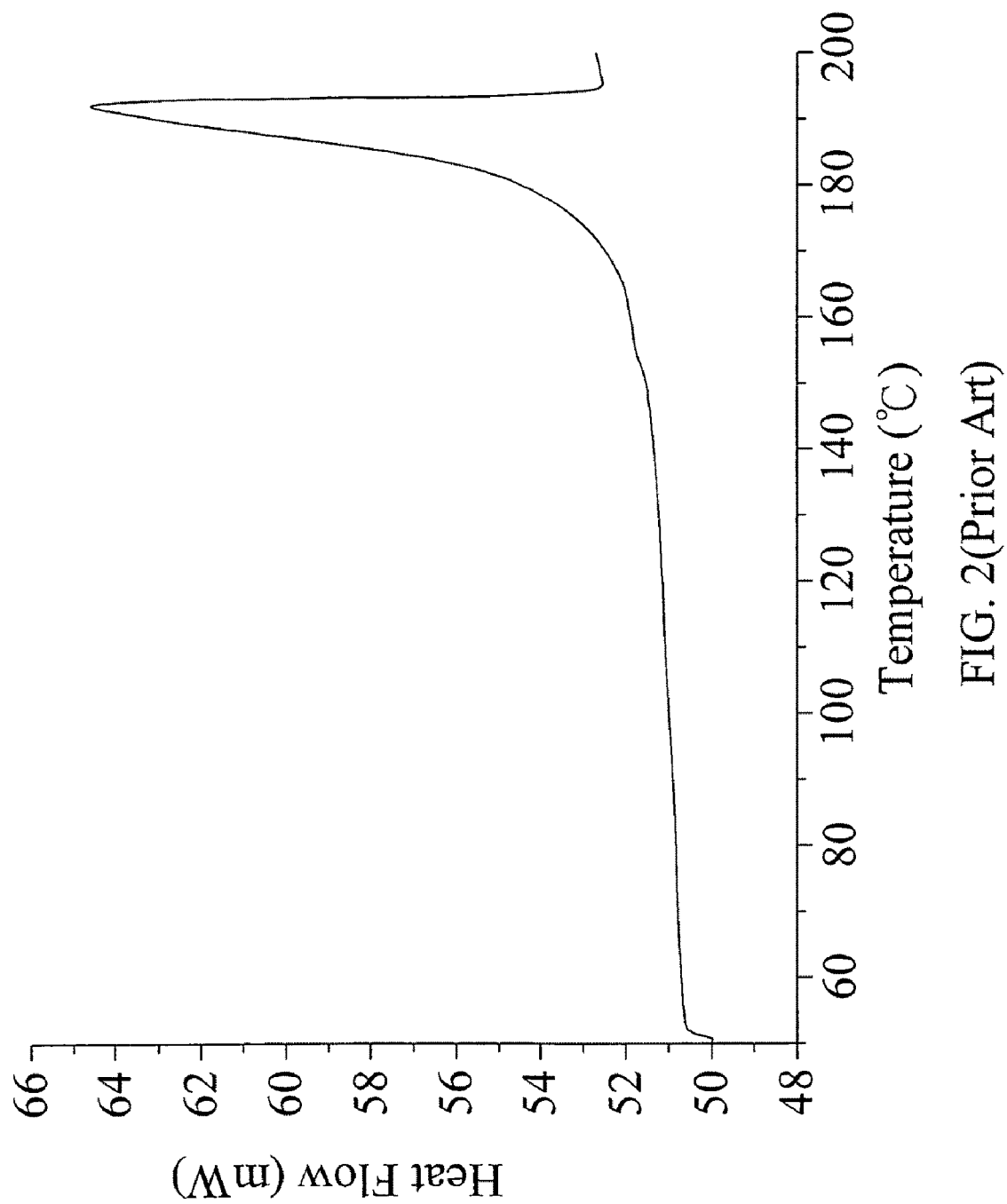
FIG. 2 is a schematic view of a differential scanning calorimetry (DSC) of a traditional Form I sucrose.
Figure 3:
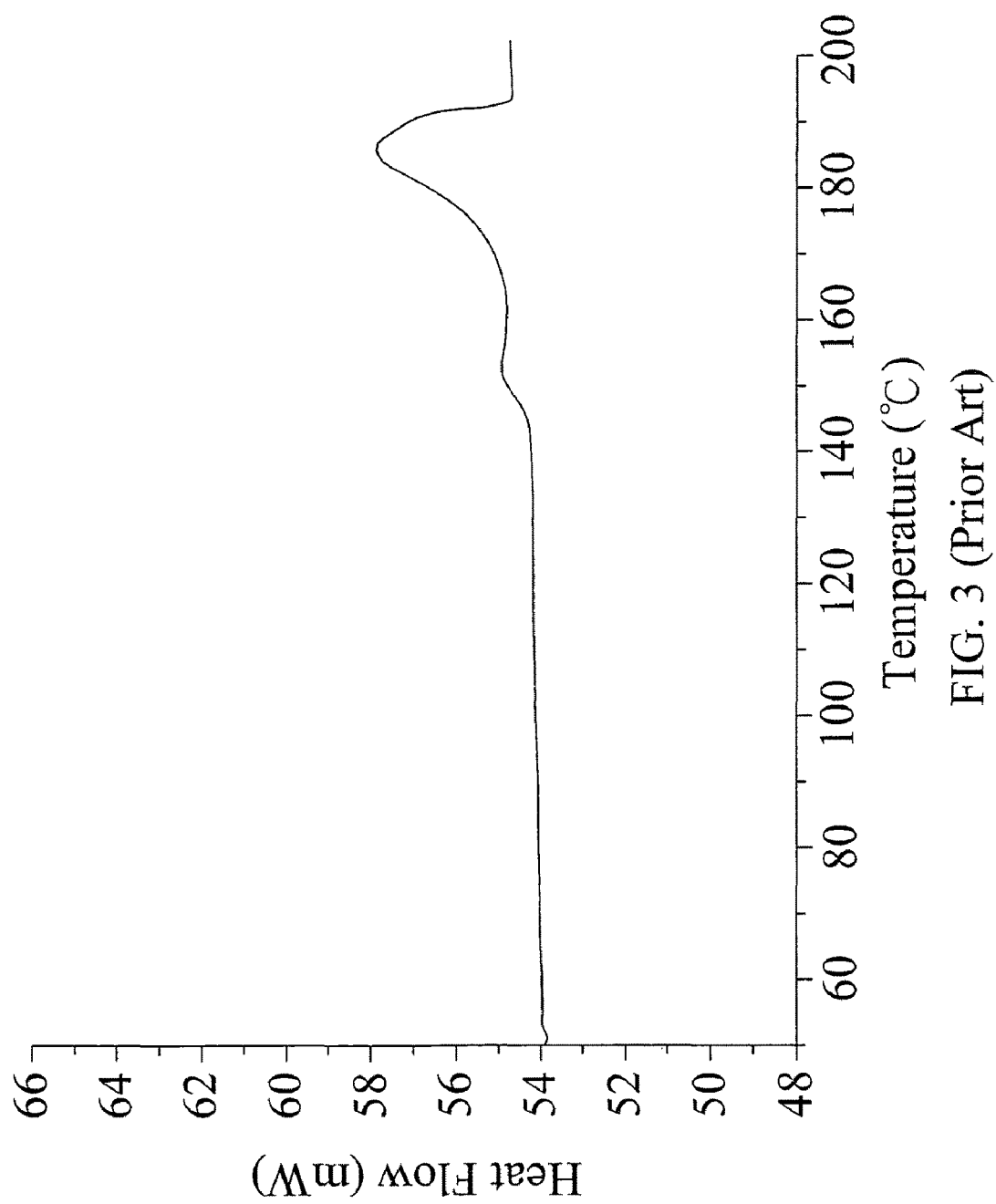
FIG. 3 is a differential scanning calorimetry (DSC) of a sucrose obtained by a conventional reverse solution method of methyl alcohol.
Figure 6:
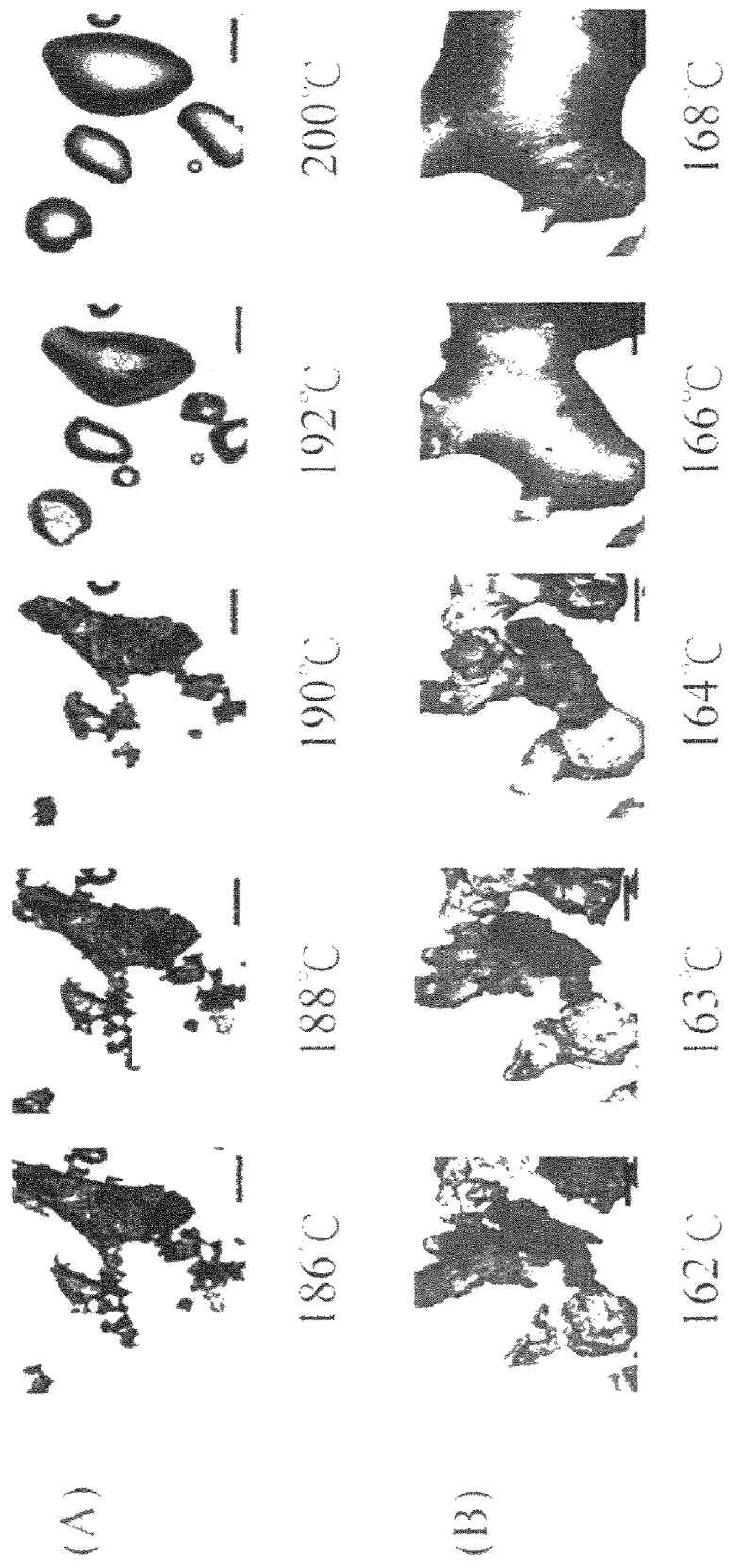
FIGS. 6A and 6B are photos of a sucrose available in the market and a sucrose of a new conformational polymorph of the present invention respectively observed by a hot-stage microscope.

The present invention further adopts a hot stage microscopy observation to examine the morph of the sucrose at a different time. FIGS. 6A and 6B are photos of a sucrose available in the market and a sucrose of a new conformational polymorph of the present invention respectively observed by the hot-stage microscope. In FIG. 6A, it is found that a general sucrose available in the market starts melting at approximately 190° C. until it is dissolved at 200° C., and this result verifies the melting point obtained by the differential scanning calorimetry (DSC) as shown in FIG. 2. However, the From II sucrose crystallized by the reverse solution method of the furfuryl alcohol in accordance with the present invention as shown in FIG. 6B has a melting point much lower than 190° C., and the modified sucrose starts melting at 163° C. and melts completely at 166° C. This result together with the result of FIG. 5 can verify that the sucrose crystallized by using furfuryl alcohol as a reverse solution in accordance with the present invention is a brand new material and completely different from a general sucrose.

In addition, the present invention uses a digital refractometer to measure a general Form I sucrose and the modified Form II sucrose recrystallized by the manufacturing method of the present invention, it is found that the two types of sucrose have substantially different solubilities, and the unmodified Form I sucrose has a solubility of 1.85-1.95 g/ml at 25° C., but the modified Form II sucrose has a solubility of 2.15-2.20 g/ml at 25° C. A power X-ray diffraction (PXRD) used in the present invention also shows that there is a slight shift of each of four peaks of the Form I sucrose and the Form II sucrose provided that 2θ equals to 28.35, 13.20, 21.01 or 28.63. The present invention further uses a thermogravimetric analyzer (TGA), a Fourier transform infrared (FT-IR) spectroscopy, a Karl Fisher (KF) titrimetry, a single crystal X-ray diffraction (SXRD), a solid state nuclear magnetic resonance (SSNMR) spectroscopy to show that the morph of the recrystallized Form II sucrose of the invention is different from the morph of the general Form I sucrose (not shown in the figure).

While the invention has been described by means of specific embodiments, numerous modifications and variations could be made thereto by those skilled in the art without departing from the scope and spirit of the invention set forth in the claims.

What is claimed is:

1. A purified Form II sucrose consisting of a single crystalline form, having a differential scanning calorimetry (DSC) result which shows one peak only, at approximately 150° C., characterized in that a reverse solution method is used to perform a reaction by adding furfuryl alcohol into a saturated Form I sucrose solution at a ratio of 1:1, wherein the Form I sucrose solution is equal to 2873 mg of sucrose per mL of water, while maintaining the reaction at 60° C., and stirring with a rotation speed of 500 rpm, such that the saturated Form I sucrose solution is recrystallized to yield the purified Form II sucrose;

wherein the purified Form II sucrose has a melting point of 140-180° C.; and wherein the purified Form II sucrose has a solubility of 2.15-2.20 g/ml at 25° C.

2. The purified Form II sucrose as recited in claim 1, wherein the purified Form II sucrose is a medicine excipient.

* * * * *